US007399294B2

(12) United States Patent
Mickley (10) Patent No.: US 7,399,294 B2
(45) Date of Patent: *Jul. 15, 2008

(54) CONTROLLED DEPTH INJECTION DEVICE

(75) Inventor: Timothy J. Mickley, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 154 days.

This patent is subject to a terminal disclaimer.

(21) Appl. No.: 10/454,624

(22) Filed: Jun. 5, 2003

(65) Prior Publication Data

US 2003/0195467 A1  Oct. 16, 2003

Related U.S. Application Data

(63) Continuation of application No. 09/633,924, filed on Aug. 8, 2000, now Pat. No. 6,613,017.

(51) Int. Cl.
    *A61M 5/00*  (2006.01)
(52) U.S. Cl. .................................................... 604/117
(58) Field of Classification Search ................ 604/117, 604/158, 164.01, 164.06, 164.07, 165.01
    See application file for complete search history.

(56) References Cited

U.S. PATENT DOCUMENTS

| 4,578,061 A | 3/1986 | Lemelson .................... 604/164 |
| 4,658,817 A | 4/1987 | Hardy ...................... 128/303.1 |
| 4,760,131 A | 7/1988 | Sundsmo et al. ........... 530/356 |
| 4,763,667 A * | 8/1988 | Manzo ........................ 600/563 |
| 4,790,311 A | 12/1988 | Ruiz ......................... 128/303.1 |
| 4,850,970 A * | 7/1989 | Sutherland ................... 604/117 |
| 4,857,057 A | 8/1989 | Sanagi |
| 4,896,671 A | 1/1990 | Cunningham et al. ....... 128/642 |
| 4,940,458 A | 7/1990 | Cohn |
| 4,973,321 A | 11/1990 | Michelson |
| 5,047,026 A | 9/1991 | Rydell ......................... 606/48 |
| 5,093,877 A | 3/1992 | Aita et al. ..................... 385/34 |
| 5,221,269 A | 6/1993 | Miller et al. |
| 5,261,889 A | 11/1993 | Laine et al. ................. 604/164 |

(Continued)

FOREIGN PATENT DOCUMENTS

DE   296 09 350 U1   10/1996

(Continued)

OTHER PUBLICATIONS

Mirhoseini et al., Abstract entitled "Transventricular Revascularization by Laser", *Lasers in Sugery and Medicine* , 2(2) 1982, 1 page.

(Continued)

*Primary Examiner*—Kevin C. Sirmons
(74) *Attorney, Agent, or Firm*—Kenyon & Kenyon LLP (57) ABSTRACT

An injection catheter assembly is provided. This assembly can include an outer elongated member having a proximal end, a distal end, and an external diameter and an inner elongated member having a proximal region and a distal region. The inner elongated member may be positioned at least partially within the outer elongated member, may have a piercing tip at the end of the proximal region and may be rotatable within the outer elongated member with the degree of rotation of the inner elongated member adjusting the distance that the piercing tip can extend from the distal end of the outer elongated member.

13 Claims, 8 Drawing Sheets

U.S. PATENT DOCUMENTS

| | | | |
|---|---|---|---|
| 5,267,982 A | 12/1993 | Sylvanowicz | |
| 5,287,861 A | 2/1994 | Wilk | 128/898 |
| 5,353,800 A | 10/1994 | Pohndorf et al. | 128/673 |
| 5,354,279 A | 10/1994 | Hofling | 604/164 |
| 5,358,485 A | 10/1994 | Vance et al. | 604/22 |
| 5,364,393 A | 11/1994 | Auth et al. | 606/34 |
| 5,370,675 A | 12/1994 | Edwards et al. | 607/101 |
| 5,380,316 A | 1/1995 | Aita et al. | 606/7 |
| 5,389,096 A | 2/1995 | Aita et al. | 606/15 |
| 5,403,311 A | 4/1995 | Abele et al. | 606/49 |
| 5,405,376 A | 4/1995 | Mulier et al. | 607/127 |
| 5,431,649 A | 7/1995 | Mulier et al. | 606/41 |
| 5,464,395 A | 11/1995 | Faxon et al. | 604/96 |
| 5,480,389 A | 1/1996 | McWha et al. | |
| 5,486,161 A | 1/1996 | Lax et al. | |
| 5,507,731 A | 4/1996 | Hernandez et al. | |
| 5,522,815 A | 6/1996 | Durgin, Jr. et al. | 606/50 |
| 5,551,427 A | 9/1996 | Altman | 128/642 |
| 5,569,220 A * | 10/1996 | Webster, Jr. | 604/527 |
| 5,569,462 A | 10/1996 | Martinson et al. | 424/424 |
| 5,591,132 A | 1/1997 | Carrie | |
| 5,591,159 A | 1/1997 | Taheri | 606/15 |
| 5,593,394 A | 1/1997 | Kanesaka et al. | |
| 5,593,405 A | 1/1997 | Osypka | 606/15 |
| 5,601,537 A | 2/1997 | Frassica | |
| 5,601,586 A | 2/1997 | Fucci et al. | 606/180 |
| 5,601,588 A | 2/1997 | Tonomura et al. | 606/185 |
| 5,607,405 A | 3/1997 | Decker et al. | 604/264 |
| 5,620,414 A | 4/1997 | Campbell, Jr. | 604/22 |
| 5,672,174 A | 9/1997 | Gough et al. | 606/41 |
| 5,681,308 A | 10/1997 | Edwards et al. | 606/41 |
| 5,683,366 A | 11/1997 | Eggers et al. | 604/114 |
| 5,697,882 A | 12/1997 | Eggers et al. | 604/114 |
| 5,700,259 A | 12/1997 | Negus et al. | 606/14 |
| 5,713,894 A | 2/1998 | Murphy-Chutorian et al. | 606/15 |
| 5,725,521 A | 3/1998 | Mueller | 606/7 |
| 5,725,523 A | 3/1998 | Mueller | 606/15 |
| 5,762,631 A | 6/1998 | Klein | |
| 5,766,164 A | 6/1998 | Mueller et al. | 606/15 |
| 5,769,843 A | 6/1998 | Abela et al. | 606/10 |
| 5,788,713 A | 8/1998 | Dubach et al. | |
| 5,797,870 A | 8/1998 | March et al. | 604/49 |
| 5,807,388 A | 9/1998 | Jeevanandam et al. | 606/15 |
| 5,810,836 A | 9/1998 | Hussein et al. | 606/108 |
| 5,827,203 A | 10/1998 | Nita | 601/2 |
| 5,840,059 A | 11/1998 | March et al. | 604/53 |
| 5,845,648 A | 12/1998 | Lemelson | |
| 5,853,409 A | 12/1998 | Swanson et al. | |
| 5,871,470 A * | 2/1999 | McWha | 604/158 |
| 5,871,495 A | 2/1999 | Mueller | 606/185 |
| 5,873,366 A | 2/1999 | Chim et al. | 128/898 |
| 5,873,855 A | 2/1999 | Eggers et al. | 604/114 |
| 5,902,289 A | 5/1999 | Swartz et al. | |
| 5,911,729 A | 6/1999 | Shikhman et al. | 606/181 |
| 5,913,853 A | 6/1999 | Loeb et al. | 606/15 |
| 5,921,982 A | 7/1999 | Lesh et al. | 606/41 |
| 5,925,033 A | 7/1999 | Aita et al. | 606/7 |
| 5,931,848 A | 8/1999 | Saadat | 606/167 |
| 5,944,716 A | 8/1999 | Hektner | 606/45 |
| 5,947,989 A | 9/1999 | Shikhman et al. | 606/180 |
| 5,964,754 A | 10/1999 | Osypka | 606/37 |
| 6,004,280 A | 12/1999 | Buck et al. | |
| 6,042,581 A | 3/2000 | Ryan et al. | 606/45 |
| 6,045,565 A | 4/2000 | Ellis et al. | 606/167 |
| 6,053,911 A | 4/2000 | Ryan et al. | 606/33 |
| 6,053,924 A | 4/2000 | Hussein | 606/108 |
| 6,056,742 A | 5/2000 | Murphy-Chutorian et al. | 606/11 |
| 6,056,743 A | 5/2000 | Ellis et al. | 606/15 |
| 6,066,126 A | 5/2000 | Li et al. | |
| 6,068,622 A | 5/2000 | Sater et al. | |
| 6,086,582 A | 7/2000 | Altman et al. | |
| 6,129,752 A | 10/2000 | Neubauer et al. | |
| 6,203,524 B1 | 3/2001 | Burney et al. | |
| 6,217,554 B1 | 4/2001 | Green | |
| 6,228,049 B1 | 5/2001 | Schroeder et al. | |
| 6,258,064 B1 * | 7/2001 | Smith et al. | 604/164.12 |
| 6,425,887 B1 | 7/2002 | McGuckin et al. | |
| 6,595,958 B1 | 7/2003 | Mickley | |
| 6,613,017 B1 * | 9/2003 | Mickley | 604/117 |
| 6,623,474 B1 * | 9/2003 | Ponzi | 604/528 |
| 2006/0200126 A1 * | 9/2006 | Mickley | 606/53 |

FOREIGN PATENT DOCUMENTS

| | | |
|---|---|---|
| DE | 195 37 081 | 4/1997 |
| DE | 195 37 084 A1 | 4/1997 |
| EP | 0 086 338 | 8/1983 |
| EP | 0 086338 * | 8/1983 |
| EP | 0 689 467 B1 | 10/1993 |
| EP | 0 692 276 | 1/1996 |
| WO | WO 96/35469 | 11/1996 |
| WO | WO 96/39963 | 12/1996 |
| WO | WO 97/18768 | 5/1997 |
| WO | WO 97/29803 | 8/1997 |
| WO | WO 97/32551 | 9/1997 |
| WO | WO 97/44071 | 11/1997 |
| WO | WO 98/05307 | 2/1998 |
| WO | WO 98/16157 | 4/1998 |
| WO | WO 98/17186 | 4/1998 |
| WO | WO 98/18391 | 5/1998 |
| WO | WO 98/27877 | 7/1998 |
| WO | WO 98/39038 | 9/1998 |
| WO | WO 99/04850 | 2/1999 |
| WO | WO 99/04851 | 2/1999 |
| WO | WO 99/29251 | 6/1999 |
| WO | WO 99/39624 | 8/1999 |
| WO | WO 99/44656 | 9/1999 |
| WO | WO 99/49773 | 10/1999 |
| WO | WO 00/09185 | 2/2000 |
| WO | WO 00/15146 | 3/2000 |
| WO | WO 00/16704 | 3/2000 |
| WO | WO 00/25850 | 5/2000 |

OTHER PUBLICATIONS

Gal et al., Abstract entitled "Analysis of Photoproducts Free Radicals and Particulate Debris Generated . . .", *Lasers in Surgery and Medicine*, 11(2) 1991, 1 page.

Isner, J., Abstract entitled "Right Ventricular Myocardial Infarction", *JAMA*, v259, n5, Feb. 5, 1988, 12 pages.

Pickering et al., Abstract entitled "Proliferative Activity in Peripheral and Coronary Atherosclerotic Plaque . . . ", *J. Clin. Invest.*, ISSN 0021-9738, Apr. 1993, 1 page.

Vineberg et al., "Creation of Intramyocardial Pathways to Channel Oxygenated Blood Between Ventricular Arteriolar Zones", *Canad. Med. Ass. J.*, vol. 96, Feb. 4, 1967, 3 pages.

Vineberg, A., "Results of 14 Years' Experience in the Surgical Treatment of Human Coronary Artery Insufficiency", *Canad. Med. Ass. J.*, vol. 92, Feb. 13, 1965, 8 pages.

Vineberg et al., "The Ivalon Sponge Procedure for Myocardial Revascularization", *Surgery*, vol. 47, No. 2, Feb. 1960, pp. 268-289.

Vineberg et al., "Treatment of Acute Myocardial Infarction by Endocardial Resection", *Surgery*, vol. 57, No. 6, Jun. 1965, pp. 832-835.

Walter et al., "Treatment of Acute Myocardial Infarction by Transmural Blood Supply from the Ventricular Cavity", *European Surgical Research*, 3:130-138 (1971).

Khazei et al., "Myocardial Canalization", *The Annals of Thoracic Surgery*, vol. 6, No. 2, Aug. 1968, pp. 163-171.

Hershey et al., "Transmyocardial Puncture Revascularization", *Geriatrics*, Mar. 1969, pp. 101-108.

Press Release dated Oct. 21, 1996, "Doctor's Demonstrate Proof of Blood Flow Through Open TMR Channels Created with PLC Systems . . . ", 1 page.

Press/News Release dated Oct. 10, 1996, "Texas Fieart Institute Presents Study Comparing the Use of CO2 . . . ", 1 page.

Goldman et al., "Nonoperative Portacaval Shunt in Swine", *Investigative Radiology*, vol. 25, No. 5, May 1990, 5 pages.

Schumacher et al., "Induction of Neoangiogenesis in Ischemic Myocardium by Human Growth Factors", *Clinical Investigation and Reports*, Dec. 1, 1997, 6 pages.

Article entitled "Gene therapy improves leg circulation—next step heart?", 70th Scientific Sessions, published on or before Nov. 2, 1998, 2 pages.

Winslow, R., "Genetic Techniques Succeed in Treating Patients with Obstructed Blood Vessels", *The Wall Street Journal*, published on or before Nov. 2, 1998, 2 pages.

Kolata, G., "Gene Therapy Gives Blood a Path Around Leg Blockages, Researchers Say", *The New York Times*, Nov. 10, 1997, 2 pages.

Mack et al., "Cardiopulmonary Support and Physiology", *The Journal of Thoracic and Cardiovascular Surgery*, vol. 115, No. 1, Jan. 1998, 10 pages.

\* cited by examiner

CONTROLLED DEPTH INJECTION DEVICE

RELATED APPLICATIONS

The present application is related to U.S. patent application Ser. No. 09/634,117, entitled "Tortuous Path Injection Device And Method" now U.S. Pat. No. 6,595,958, U.S. patent application Ser. No. 09/635,083, entitled "Cather Shaft Assembly," and is a continuation of U.S. patent application Ser. No. 09/633,924, now U.S. Pat. No. 6,613,017.

RELATED FIELD

The present invention relates generally to devices and methods for delivering therapeutic or diagnostic agents to a portion of the human body. More particularly, the present invention relates generally to devices and methods for delivering and injecting fluid into heart tissue.

BACKGROUND

Intravascular catheters are currently utilized in a wide variety of minimally invasive or percutaneous medical procedures. Generally, an intravascular catheter enables a physician to remotely perform a medical procedure by inserting the catheter into the vascular system of the patient at an easily accessible location and navigating the tip of the catheter to a desirable target site. By this method, virtually any target site in the patient's vascular system may be remotely accessed.

Typically, a percutaneous procedure begins with the step of inserting a distal portion of the catheter into the patient's vasculature at a convenient location. Once the distal portion of the catheter has entered the patient's vascular system the physician may urge the distal tip forward by applying longitudinal forces to the proximal portion of the catheter. Frequently the path taken by a catheter through the vascular system is tortuous, requiring the catheter to change direction frequently. While advancing the catheter through the tortuous path of the patient's vasculature, the physician must steer the distal end of the catheter. During a percutaneous procedure, the physician typically is not able to manipulate the distal portion of the catheter directly. For this reason, physicians typically must steer the distal end of the catheter by applying torsional forces to the proximal portion of the catheter.

Injection catheters are a type of catheter which may be used to inject therapeutic or diagnostic agents into various target tissues within the human body. An advantage of injection catheters is that the target tissue may be accessed utilizing minimally invasive surgical techniques. As with other types of catheters, the physician typically is not able to manipulate the distal portion of an injection catheter directly.

In many applications the target tissue is within a wall of an organ such as the stomach or the heart. When the target tissue is within the wall of an organ it is often desirable to inject the therapeutic or diagnostic agent into the tissue proximate the center of the organ wall. If the needle of the injection catheter inadvertently passes through the wall, the therapeutic or diagnostic agents dispensed from the distal end of the needle will not be effectively delivered to the target tissue. Wall thickness may vary from organ to organ. Additionally, wall thickness may vary within one organ.

One example of a medical procedure involving the delivery of a therapeutic and/or diagnostic agent to a targeted portion of a patient's body is the treatment of esophageal varices. This is a condition in which blood vessels of the esophagus are enlarged and may potentially burst. For such a procedure, a therapeutic agent is injected into the varix. When treating an esophageal varix, the agent may be a coagulant such as sodium morrhuate. When a coagulant is injected into a varix, it causes it to occlude. An injection catheter may be used to deliver the therapeutic agent in order to minimize the invasive nature of the procedure.

In a similar procedure, an injection catheter may be utilized in the treatment of ulcers in the stomach lining. With such treatment, an injection catheter may be used to deliver drugs such as sclerosing or vasoconstrictive agents. These drugs typically clot or occlude the bleeding tissue to stop bleeding or to reduce the possibility of a blood vessel bursting.

Injection catheters may also be used to inject therapeutic or diagnostic agents into the heart. Examples of agents delivered to the heart include genes, proteins, or drugs. In the case of injecting a therapeutic agent into the heart, 27 or 28 gauge needles are generally used to inject solutions carrying genes, proteins, or drugs directly into the myocardium. A typical volume of an agent delivered to an injection site is about 100 microliters.

Therapeutic and diagnostic agents may be delivered to a portion of the heart as part of a percutaneous myocardial revascularization (PMR) procedure. PMR is a procedure which is aimed at assuring that the heart is properly oxygenated. Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The tortuous path and small diameter of these blood vessels limit access to the stenotic lesions. The sheer number and small size of these stenotic lesions make techniques such as cardiovascular by-pass surgery, angioplasty, and atherectomy impractical.

When techniques which treat individual lesions are not practical percutaneous myocardial revascularization (PMR) may be used to improve the oxygenation of the myocardial tissue. A PMR procedure generally involves the creation of holes, craters or channels directly into the myocardium of the heart. In a typical PMR procedure, these holes are created using radio frequency energy delivered by a catheter having one or more electrodes near its distal end. After the wound has been created, therapeutic agents are sometimes ejected into the heart chamber from the distal end of a catheter.

Positive clinical results have been demonstrated in human patients receiving PMR treatments. These results are believed to be caused in part by blood flowing within a heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenesis. After the wound has been created, therapeutic agents which are intended to promote angiogenesis are sometimes ejected into the heart chamber. A limitation of this procedure is that the therapeutic agent may be quickly carried away by the flow of blood through the heart.

In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

SUMMARY OF THE INVENTION

The present invention relates generally to devices and methods for delivering therapeutic or diagnostic agents to a portion of the human body. More particularly, the present invention relates generally to devices and methods for delivering and injecting fluid into heart tissue.

An injection catheter in accordance an exemplary embodiment of the present invention includes a first elongate shaft having a lumen and a second elongate shaft disposed within the lumen of the first elongate shaft. In this exemplary embodiment, the second elongate shaft includes a point and an injection orifice proximate its distal end. In many applications it is desirable to advance the distal end of the second elongate shaft by a known distance relative to the distal end of the first elongate shaft. For example, this known displacement may be desirable when a physician wishes to inject a fluid into the wall of an organ.

In one embodiment, a knob is fixed to the second elongate shaft of the exemplary injection catheter proximate a proximal end thereof. Also in this embodiment, a housing is disposed about the first elongate shaft of the exemplary injection catheter proximate the proximal end thereof. A physician utilizing the catheter in a surgical procedure may advance the distal end of the second elongate shaft by rotating the second elongate shaft relative to the first elongate shaft. To facilitate this relative rotation, the physician may grasp the housing and apply a torque to the knob.

In a particularly preferred embodiment, there is a known relationship between the rotary motion of the second elongate shaft relative to the first elongate shaft and the linear motion of the second elongate shaft relative to the first elongate shaft. For example, the physician may advance the second elongate shaft by a desired distance by rotating the second elongate shaft by a corresponding number of turns.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases., the drawings may be highly diagrammatic in nature. Examples of constructions, materials, dimensions, and manufacturing processes are provided for various elements. Those skilled in the art will recognize that many of the examples provided have suitable alternatives which may be utilized.

Figure 1:
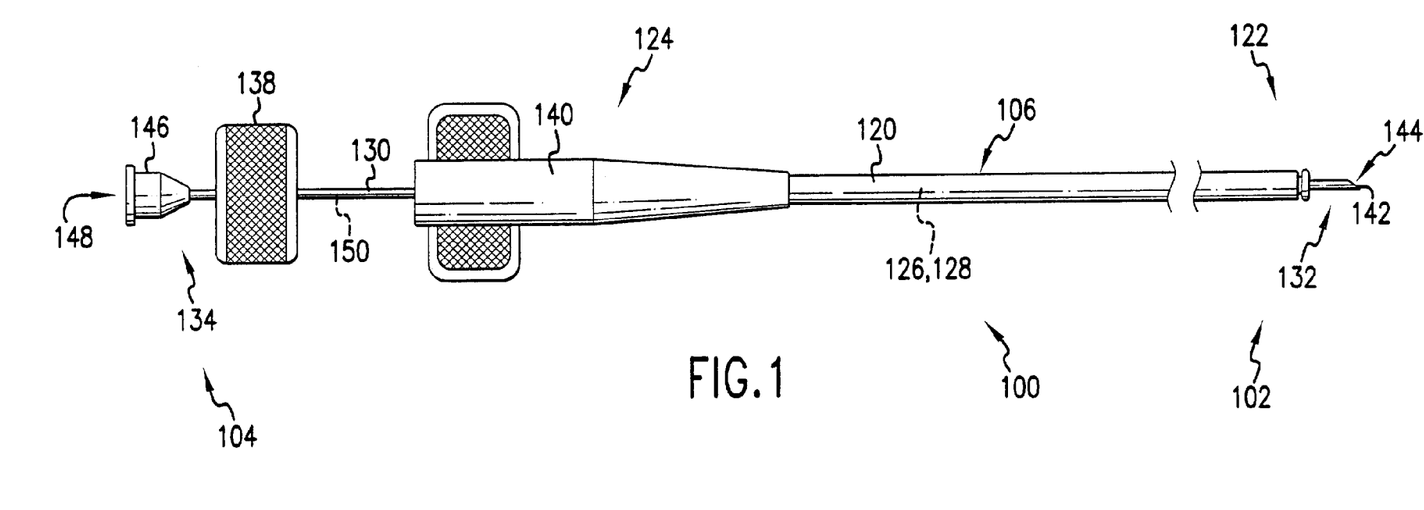
FIG. 1 is a plan view of a catheter in accordance with an exemplary embodiment of the present invention.

FIG. 1 is a plan view of a catheter 100 in accordance with the present invention. Catheter 100 has a distal end 102, a proximal end 104, and a shaft assembly 106. Shaft assembly 106 comprises a first elongate shaft 120 having a distal end 122, a proximal end 124, and an inside surface 126 defining a lumen 128. Shaft assembly 106 also includes a second elongate shaft 130 disposed within lumen 128 of first elongate shaft 120.

Second elongate shaft 130 has a distal end 132 and a proximal end 134. In many applications it is desirable to advance distal end 132 of second elongate shaft 130 by a known distance relative to distal end 122 of first elongate shaft 120. In the embodiment of FIG. 1, a knob 138 is fixed to second elongate shaft 130. Also in the embodiment of FIG. 1, a housing 140 is disposed about first elongate shaft 120 proximate proximal end 124 thereof. In a preferred embodiment, a physician utilizing catheter 100 in a surgical procedure may advance distal end 132 of second elongate shaft 130 by rotating second elongate shaft 130 relative to first elongate shaft 120. To facilitate this relative rotation, the physician may grasp housing 140 and apply a torque to knob 138.

In a particularly preferred embodiment, there is a known relationship between the rotary motion of second elongate shaft 130 relative to first elongate shaft 120 and the linear motion of second elongate shaft 130 relative to first elongate shaft 120. For example, the physician may advance second elongate shaft 130 by a desired distance by rotating second elongate shaft 130 by a corresponding number of turns.

In the embodiment of FIG. 1, second elongate shaft 130 forms a point 142 proximate distal end 132 thereof. Second elongate shaft 130 also defines an injection port 144 proximate point 142. A hub 146 is disposed about second elongate shaft 130. Hub 146 defines a proximal port 148. In a preferred embodiment, proximal port 148 is in fluid communication with injection port 144 via an injection lumen 150 defined by second elongate shaft 130.

Catheter 100 of FIG. 1 may be generally referred to as an injection catheter. It is to be appreciated that a catheter in accordance with the present invention may comprise various types of catheters without deviating from the spirit and scope of the present invention.

In a preferred embodiment, second elongate shaft 130 of catheter 100 comprises hypodermic tubing. Second elongate shaft 130 may comprise various metallic and non-metallic materials without deviating from the spirit and scope of the present invention. Examples of metallic materials which may be suitable in some applications include stainless steel, and nickel-titanium alloy. Examples of non-metallic materials which may be suitable in some applications are included in the list below which is not exhaustive: polycarbonate, poly (L-lactide) (PLLA), poly(D,L-lactide) (PLA), polyglycolide (PGA), poly(L-lactide-co-D,L-lactide) (PLLA/PLA), poly (L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly (phosphate ester), poly(amino acid), poly(hydroxy butyrate), polyacrylate, polyacrylamid, poly(hydroxyethyl methacrylate), polyurethane, polysiloxane and their copolymers.

In a preferred embodiment, first elongate shaft 120 of catheter 100 comprises an elongate tubular member including a reinforcement member (e.g., braided or coiled wire). Second elongate shaft 130 may comprise various metallic and non-metallic materials without deviating from the spirit and scope of the present invention. Examples of metallic materials which may be suitable in some applications include stainless steel, and nickel-titanium alloy. Examples of non-metallic materials which may be suitable in some applications include: polyethylene (PE), polypropylene (PP), polyvinylchloride (PVC), polyurethane, polytetrafluoroethylene (PTFE), polyether block amide (PEBA), polyamide, and polyimide.

Figure 2:
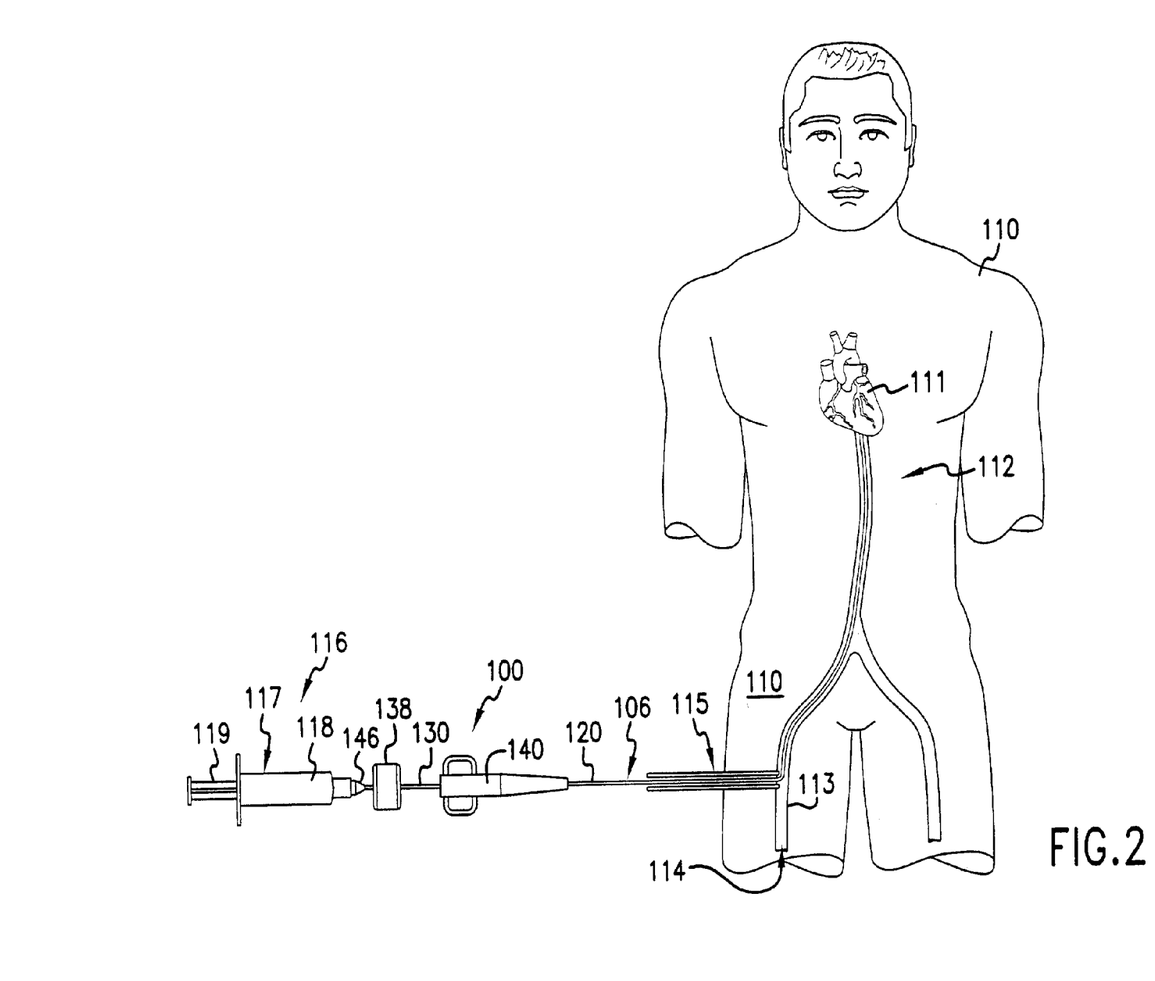
FIG. 2 is a diagrammatic view including the catheter of FIG. 1 and a patient having a heart and a vascular system including a blood vessel defining a blood vessel lumen.

FIG. 2 is a diagrammatic view including catheter 100 of FIG. 1 and a patient 110. Patient 110 has a heart 111 and a vascular system 112 including a blood vessel 113 defining a blood vessel lumen 114. An access sheath 115 is partially disposed within a leg of patient 110. A distal end of access sheath 115 is disposed within blood vessel lumen 114 of blood vessel 113. Access sheath 115 may aid in the introduction of catheter 100 into blood vessel lumen 114.

As shown in FIG. 2, a portion of catheter 100 is disposed within blood vessel lumen 114 of blood vessel 113. Distal end 102 (not visible in FIG. 2) of catheter 100 is disposed within heart 111 of patient 110. In a preferred embodiment, distal end 102 of catheter 100 is disposed proximate a wall of heart 111.

In the embodiment of FIG. 2, a fluid source 116 is coupled to hub 146 disposed about second elongate shaft 130 of catheter 100. In the embodiment of FIG. 2, fluid source 116 includes a variable volume chamber 117 defined by a body 118. In a preferred embodiment, variable volume chamber 117 is in fluid communication with injection lumen 150 of second elongate shaft 130. A plunger 119 is slidingly disposed within variable volume chamber 117. Urging the plunger distally has the effect of urging fluid into injection lumen 150 of second elongate shaft 130. A number of energy sources may be utilized to urge plunger 119 distally. Energy sources which may be suitable in some applications include springs, compressed gas, a human being, and electricity. Various additional embodiments of fluid source 116 are possible without deviating from the spirit and scope of the present invention. Examples of fluid sources which may be suitable in some applications include syringes, peristaltic pumps, and an I.V. bag with pressure applied to its outer surface.

A method of injecting a fluid into heart 111 of patient 110 may be described with reference to FIG. 2. The distal end of access sheath 115 may be inserted into blood vessel lumen 114 of blood vessel 113. Distal end 102 of catheter 100 may be inserted into the lumen of access sheath 115. Distal end 102 of catheter 100 may be advanced through access sheath 115 and into blood vessel lumen 114 of blood vessel 113. Catheter 100 may be urged forward through vascular system 112 of patient 110 until distal end 102 is proximate the target tissue (e.g., a wall of heart 111). In FIG. 2 it may be appreciated that shaft assembly 106 of catheter 100 is bent in a plurality of locations to conform with a tortuous path defined by vascular system 112.

In a preferred method, distal end 132 of second elongate shaft 130 is disposed within lumen 128 of first elongate shaft 120 during the above steps. Once distal end 102 of catheter 100 is positioned proximate the target tissue, second elongate shaft 130 may be advanced so that point 142 penetrates the bodily tissue at the target site. With injection port 144 of second elongate shaft 130 disposed within the target tissue, fluid may be urged into the target tissue. For example, force may be applied to plunger 119 urging fluid out of fluid source 116 and into injection lumen 150 of second elongate shaft 130. The addition of fluid from fluid source 116 results in the injection of fluid into the target tissue.

In many applications it is desirable to advance point 142 and injection port 144 into the target tissue by a known distance. A physician may advance point 142 and injection port 144 into the target tissue by rotating knob 138. The physician may determine the depth of penetration, for example, by observing the angle of rotation of knob 138 relative to housing 140 disposed about second elongate shaft 130. Embodiments have been envisioned in which knob 138 and/or housing 140 include indicia to aid the physician.

The fluid injected into the target area may include various therapeutic or diagnostic agents adapted to treat the medical condition which the physician is treating. It is to be appreciated that methods in accordance with the present invention may be used in the treatment of a number of medical conditions. For example, methods and devices of performing percutaneous myocardial revascularization (PMR) in accordance with the present invention have been envisioned. For example, a plurality of wounds may be created in hibernating tissue of the heart. These wounds maybe created by injecting a fluid into the tissue of the heart. As a result of these wounds, there will be increased blood flow to the myocardium caused in part by the body's healing response to the wound. One healing response of the body is sometimes referred to as angiogenesis. In addition to promoting increased blood flow, it is also believed that PMR improves a patient's condition through denervation. Denervation is the elimination of nerves. The creation of wounds during this procedure results in the elimination of nerve endings which were previously sending pain signals to the brain as a result of hibernating tissue.

Suitable wounds may be created by injecting a fluid such as water, saline, or Ringer's solution into the heart tissue. Wound formation and revascularization of myocardial tissue may be enhanced by injecting a fluid including a therapeutic agent into the tissue of the heart. Examples, of therapeutic agents which may be suitable include growth factors, drugs and caustic agents. The fluid injected into the heart tissue may also include a radiopaque material. Injecting a radiopaque material into the wound effectively marks the locations which have been treated. This will aid the physician in procedures which are being performed percutaneously using fluoroscopic equipment.

In the exemplary embodiment of FIG. 2, catheter 100 may be utilized to inject fluid into heart 111 of patient 110. It is to be appreciated that catheter 100 may be utilized in the treatment various medical conditions occurring in various locations in the body. For example, catheter 100 may be used in the treatment of esophageal varices, a condition in which blood vessels of the esophagus are enlarged and may potentially burst. For such a procedure, injection port 144 would be disposed proximate the enlarged varix and an appropriate agent would be injected into the varix. When treating an esophageal varice, the agent may be coagulant such as sodium morrhuate. When a coagulant is injected into a varix, it causes the occlusion thereof.

Figure 3:
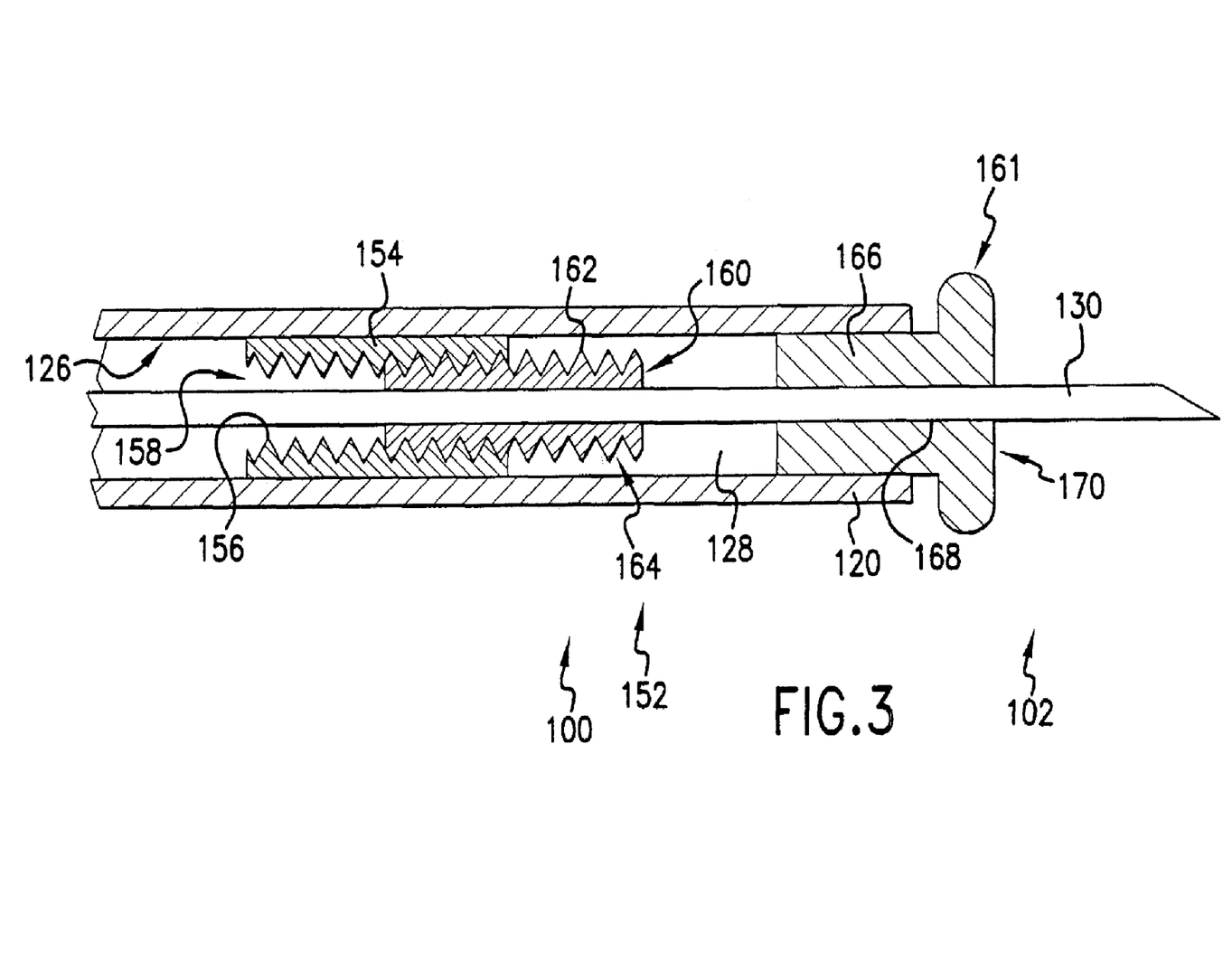
FIG. 3 is a cross sectional view of a distal portion of the catheter of FIG. 1 and FIG. 2.

FIG. 3 is a cross sectional view of a distal portion 152 of catheter 100 of FIG. 1 and FIG. 2. In FIG. 3 it may be appreciated that catheter 100 includes a first helical member 154 comprising a plurality of turns 156 disposed within lumen 128 of first elongate shaft 120. In a preferred embodiment, first helical member 154 is fixed to inside surface 126 of first elongate shaft 120. In the embodiment of FIG. 3, first helical member 154 comprises a first screw thread 158.

Also in the embodiment of FIG. 3, a second helical member 160 comprising a plurality of turns 162 is disposed about second elongate shaft 130. In the embodiment of FIG. 3, second helical member 160 is preferably fixed to second elongate shaft 130. In the embodiment of FIG. 3, second helical member 160 comprises a second screw thread 164. In FIG. 3, it may be appreciated that a plurality of turns 162 of second helical member 160 are disposed between a plurality of turns 156 of first helical member 154.

In the embodiment of FIG. 3, a header 166 is partially disposed within lumen 128 of first elongate shaft 120. In a preferred embodiment, header 166 includes a radial enlargement 161. In this preferred embodiment, radial enlargement 161 provides a generally enlarged distal contact surface 170. Generally enlarged distal contact surface 170 reduces the likelihood that undesired tissue damage will occur when distal end 102 of catheter 100 is urged against bodily tissue. Header 166 also defines a header lumen 168. As shown in FIG. 3, second elongate shaft 130 is slidingly disposed within header lumen 168.

Figure 4:
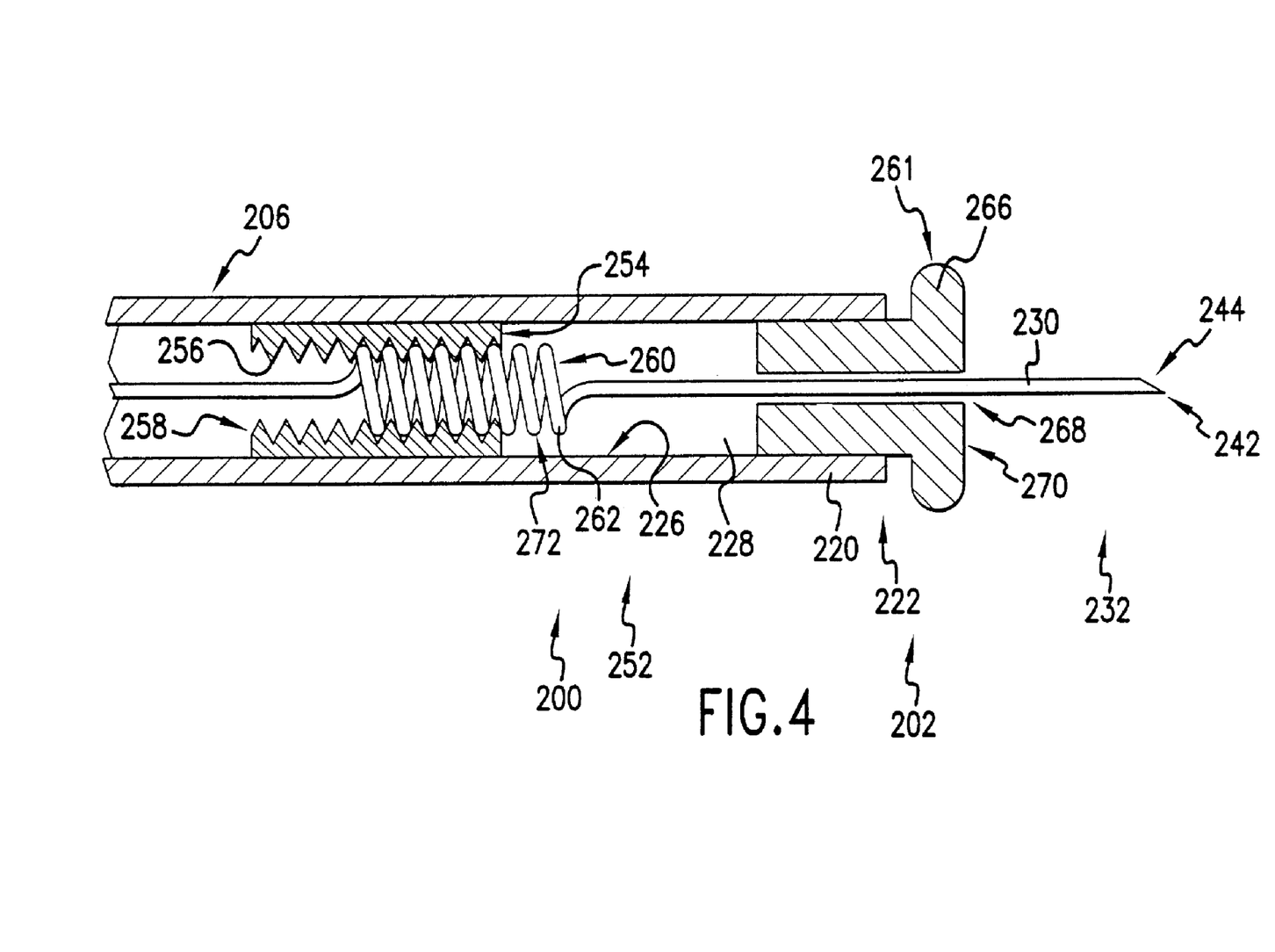
FIG. 4 is a partial cross sectional view of a distal portion of an additional exemplary embodiment of a catheter in accordance with the present invention.

FIG. 4 is a partial cross sectional view of a distal portion 252 of an additional embodiment of a catheter 200 in accordance with the present invention. Catheter 200 includes a shaft assembly 206 comprising a first elongate shaft 220 having a distal end 222 and an inside surface 226 defining a lumen 228. Shaft assembly 206 also includes a second elongate shaft 230 having a distal end 232 slidingly disposed within lumen 228 of first elongate shaft 220.

In many applications it is desirable to advance distal end 232 of second elongate shaft 230 by a known distance relative to distal end 222 of first elongate shaft 220. In the embodiment of FIG. 4, second elongate shaft 230 may be selectively advanced and retracted.

In FIG. 4 it may be appreciated that catheter 200 includes a first helical member 254 comprising a plurality of turns 256 disposed within lumen 228 of first elongate shaft 220. In the embodiment of FIG. 4, first helical member 254 is preferably fixed to inside surface 226 of first elongate shaft 220. In the embodiment of FIG. 4, first helical member 254 comprises a first screw thread 258. Embodiments of the present invention have been envisioned in which first helical member 254 comprises a rib formed by first elongate shaft. Embodiments of the present invention have also been envisioned in which first helical member 254 comprises a coil.

A second helical member 260 is formed by second elongate shaft 230. In the embodiment of FIG. 4, second helical member 260 comprises a coil 272 having a plurality of turns 262. In FIG. 4, it may be appreciate that a plurality of turns 262 of second helical member 260 are disposed between a plurality of turns 256 of first helical member 254.

In the embodiment of FIG. 4, a header 266 is partially disposed within lumen 228 of first elongate shaft 220. In a preferred embodiment, header 266 includes a radial enlargement 261. In this preferred embodiment, radial enlargement 261 provides a generally enlarged distal contact surface 270. Generally enlarged distal contact surface 270 reduces the likelihood that undesired tissue damage will occur when distal end 202 of catheter 200 is urged against bodily tissue. Header 266 also defines a header lumen 268. As shown in FIG. 4, second elongate shaft 230 is slidingly disposed within header lumen 268.

In the embodiment of FIG. 4, second elongate shaft 230 forms a point 242 proximate distal end 232 thereof. Second elongate shaft 230 also defines an injection port 244 proximate point 242. A physician may advance point 242 and injection port 244 of second elongate shaft 230 into a target tissue by rotating second elongate shaft 230. In a particularly preferred embodiment, there is a known relationship between the rotary motion of second elongate shaft 230 relative to first elongate shaft 220 and the linear motion of second elongate shaft 230 relative to first elongate shaft 220. For example, the physician may advance point 242 and injection port 244 of second elongate shaft 230 by a desired distance by rotating second elongate shaft 230 by a corresponding number of turns.

Figure 5:
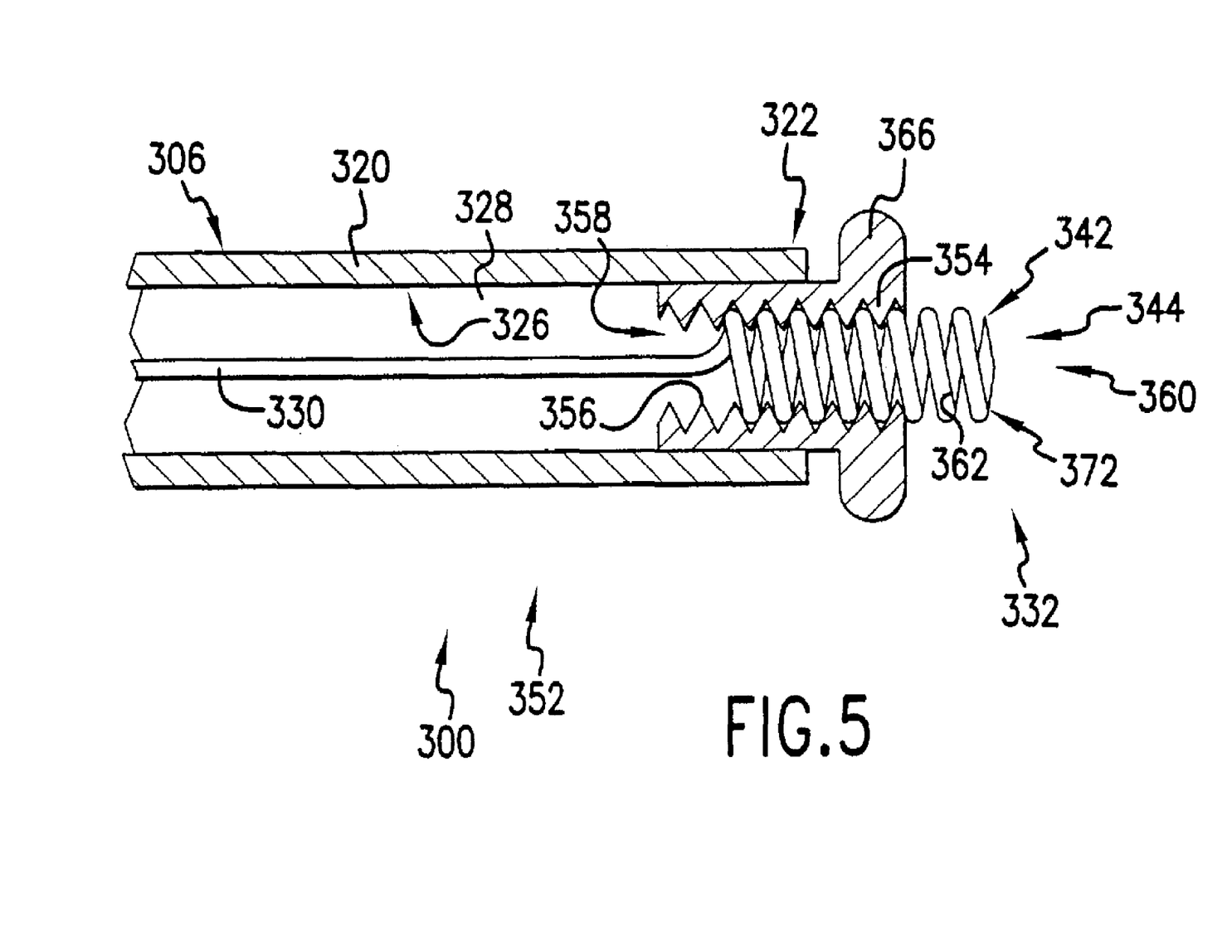
FIG. 5 is a partial cross sectional view of a distal portion of an additional exemplary embodiment of a catheter in accordance with the present invention.

FIG. 5 is a partial cross sectional view of a distal portion 352 of an additional embodiment of a catheter 300 in accordance with the present invention. Catheter 300 includes a shaft assembly 306 comprising a first elongate shaft 320 having a distal end 322 and an inside surface 326 defining a lumen 328. A header 366 is partially disposed within lumen 328 of first elongate shaft 320 proximate distal end 322. Header 366 includes a first helical member 354 comprising a plurality of turns 356. In the embodiment of FIG. 5, first helical member 354 comprises a first screw thread 358.

A second elongate shaft 330 is partially disposed within lumen 328 of first elongate shaft 320. Second elongate shaft 330 forms a second helical member 360. In the embodiment of FIG. 5, second helical member 360 comprises a coil 372 having a plurality of turns 362. In FIG. 5, it may be appreciated that a plurality of turns 362 of second helical member 360 are disposed between a plurality of turns 356 of first helical member 354. A distal end 332 of second elongate shaft 330 may be advanced into a target tissue by rotating second elongate shaft 330. In a particularly preferred embodiment, there is a known relationship between the rotary motion of second elongate shaft 330 relative to first elongate shaft 320 and the linear motion of second elongate shaft 330 relative to first elongate shaft 320. For example, the physician may advance point 342 and injection port 344 of second elongate shaft 330 by a desired distance by rotating second elongate shaft 330 by a corresponding angle.

Figure 6:
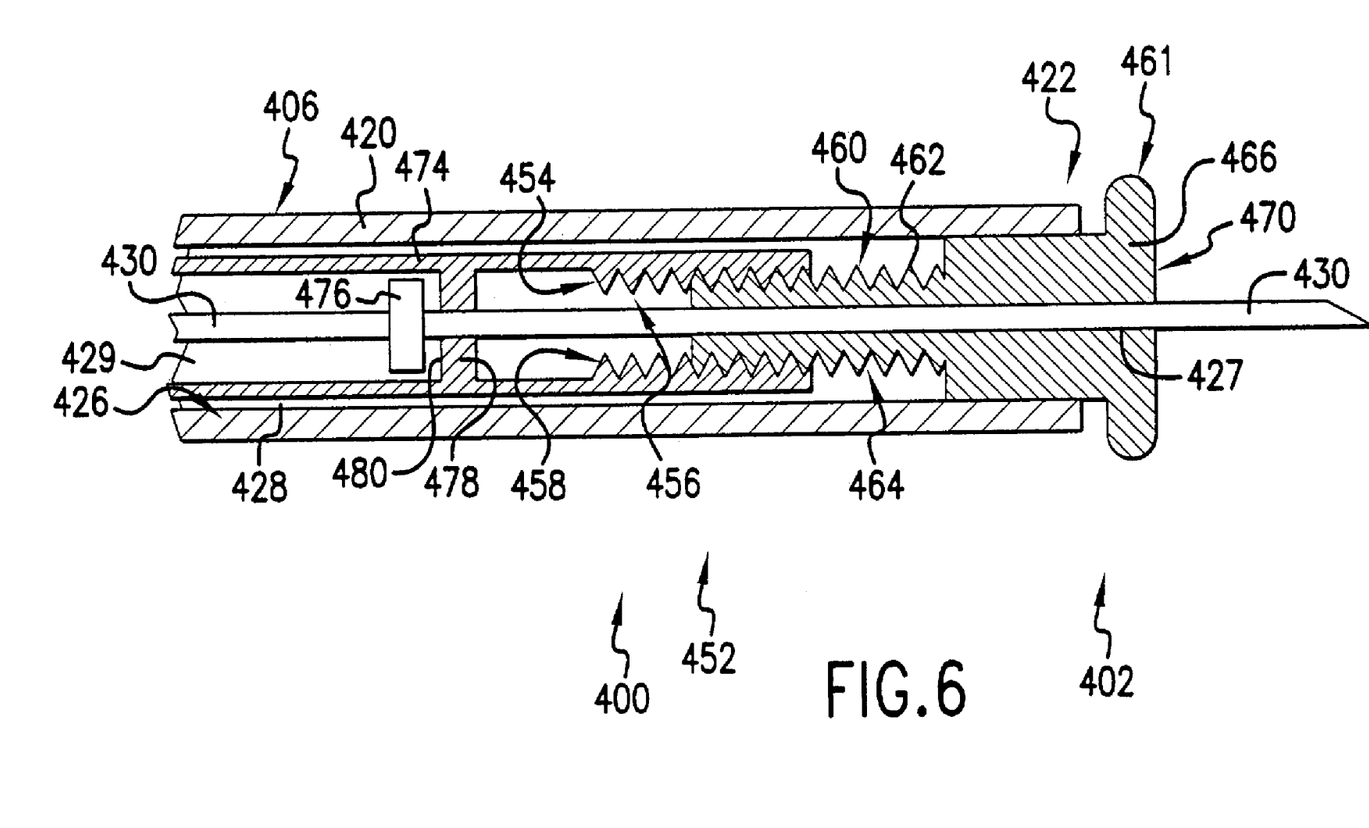
FIG. 6 is a partial cross sectional view of a distal portion of an additional exemplary embodiment of a catheter in accordance with the present invention.

FIG. 6 is a partial cross sectional view of a distal portion 452 of an additional embodiment of a catheter 400 in accordance with the present invention. Catheter 400 includes a shaft assembly 406 comprising a first elongate shaft 420, a second elongate shaft 430, and a third elongate shaft 474. First elongate shaft 420 has a distal end 422 and an inside surface 426 defining a lumen 428. Third elongate shaft 474 is disposed within lumen 428 of first elongate shaft 420. Second elongate shaft 430 is disposed within a third lumen 429 defined by third elongate shaft 474.

In the embodiment of FIG. 6, a header 466 is partially disposed within lumen 428 of first elongate shaft 420. In a preferred embodiment, header 466 includes a radial enlargement 461. In this preferred embodiment, radial enlargement 461 provides a generally enlarged distal contact surface 470. Generally enlarged distal contact surface 470 reduces the likelihood that undesired tissue damage will occur when distal end 402 of catheter 400 is urged against bodily tissue. Header 466 also defines a header lumen 427. As shown in FIG. 6, second elongate shaft 430 is slidingly disposed within header lumen 427.

A first helical member 454 comprising a plurality of turns 456 is disposed within third lumen 429 of third elongate shaft 474. In the embodiment of FIG. 6, first helical member 454 comprises a first screw thread 458. First helical member 454 is adapted to threadingly engage a second helical member 460 having a plurality of turns 462. As shown in FIG. 6, second helical member 460 is formed by a portion of header 466. Header 466 is partially disposed within lumen 428 of first elongate shaft 420. In the embodiment of FIG. 6, second helical member 460 comprises a second screw thread 464. Header 466 also defines a header lumen 427. As shown in FIG. 6, second elongate shaft 430 is disposed within header lumen 427.

In the embodiment of FIG. 6, a flange 476 is disposed about second elongate shaft 430. Third elongate shaft 474 includes a stop 478. In a presently preferred embodiment, stop 478 and flange 476 are adapted to limit the longitudinal travel of second elongate shaft 430 relative to first elongate shaft 420.

Third elongate shaft 474 may be utilized to adjust the depth of injection during a surgical procedure. A physician may apply a rotational force to a proximal end of third elongate shaft 474 causing it to rotate relative to header 466. In a preferred embodiment, rotation of third elongate shaft 474 will alter the distance between a proximal surface 480 of stop 478 and distal contact surface 470 of header 466. It may be appreciated that a change in the distance between a proximal surface 480 of stop 478 and distal contact surface 470 of header 466 will result in a change in the depth of injections made with catheter 400. In the embodiment of FIG. 6, the travel of second elongate shaft 430 preferably stops when flange 476 contacts stop 478.

Figure 7:
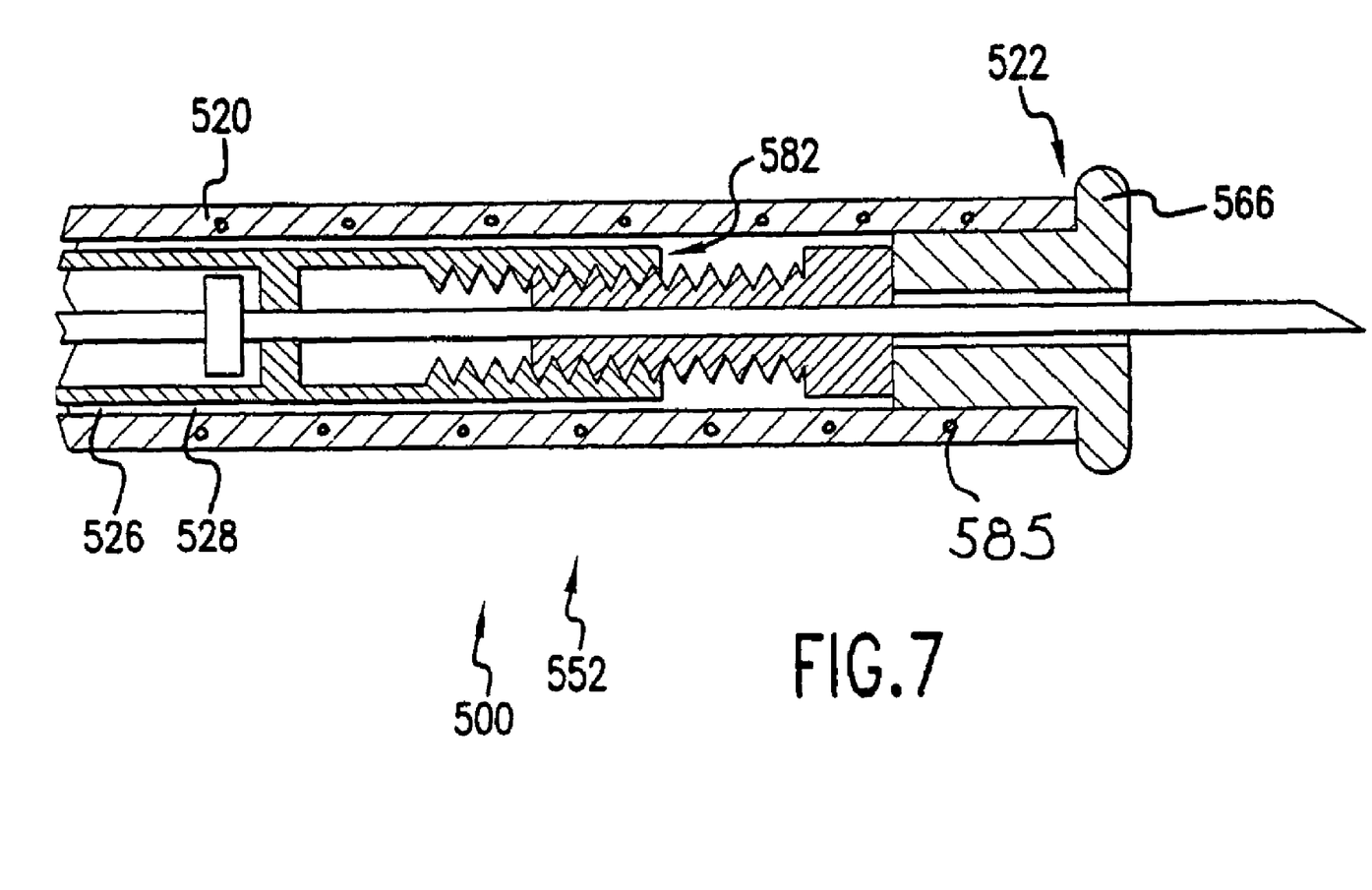
FIG. 7 is a partial cross sectional view of a catheter having an inner assembly in accordance with an exemplary embodiment of the present invention.

FIG. 7 is a partial cross sectional view of a distal portion 552 of an additional embodiment of a catheter 500 in accordance with the present invention. Catheter 500 includes a first elongate shaft 520 having a distal end 522 and an inside surface 526 defining a lumen 528. A header 566 is partially disposed within lumen 528 of first elongate shaft 520 proximate the distal end thereof. An inner assembly 582 is slidingly disposed within lumen 528 of first elongate shaft 520.

Figure 8:
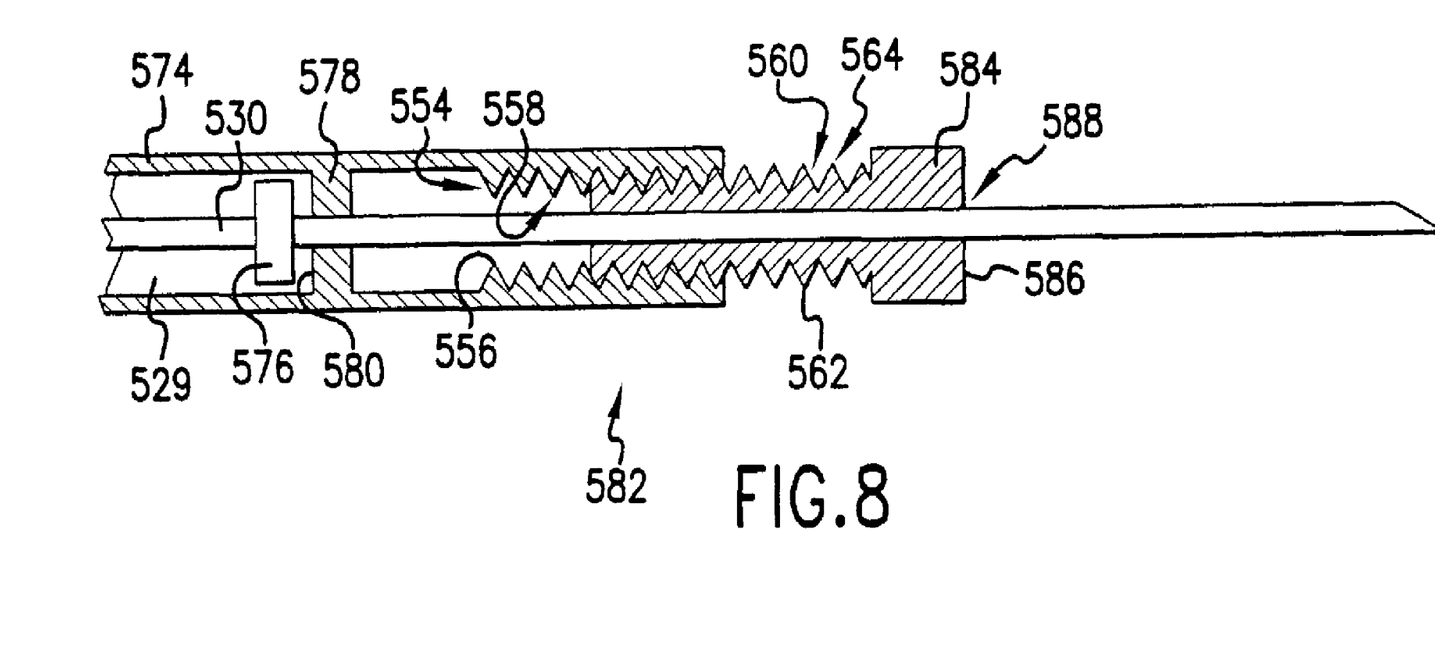
FIG. 8 is a partial cross sectional view of the inner assembly of FIG. 7.

FIG. 8 is a partial cross sectional view of inner assembly 582 of FIG. 7. In the embodiment of FIG. 8, inner assembly 582 has been withdrawn from lumen 528 of first elongate shaft 520. Inner assembly 582 includes a third elongate shaft 574, a second elongate shaft 530, and a ferrule 584. Second elongate shaft 530 is partially disposed within a third lumen 529 defined by third elongate shaft 574.

Third or outer elongate shaft 574 of inner assembly 582 includes a first helical member 554. Ferrule 584 of inner assembly 582 includes a second helical member 560. In the embodiment of FIG. 8, first helical member 554 and second helical member 560 comprise a first screw thread 558 and a second screw thread 564 respectively. A plurality of turns 556 of first helical member 554 are disposed in threaded engagement with a plurality of turns 562 of second helical member 560.

Ferrule 584 includes a distal end 586 and a ferrule lumen 588. Ferrule lumen 588 allows second elongate shaft 530 to extend through ferrule 584. In the embodiment of FIG. 8, a flange 576 is disposed about second elongate shaft 530. Third elongate shaft 574 includes a stop 578. In a preferred embodiment, stop 578 and flange 576 are adapted to limit the longitudinal travel of distal end 532 of second elongate shaft 530 relative to distal end 586 of ferrule 584.

Inner assembly 582 may be utilized to adjust the depth of injection during a surgical procedure. For example, a physician may withdraw inner assembly 582 from catheter 500 and rotate ferrule 584 relative to third elongate shaft 574. In a preferred embodiment, relative rotation between third elongate shaft 574 and ferrule 584 will alter the distance between a proximal surface 580 of stop 578 and distal end 586 of ferrule 584. It may be appreciated that a change in the distance between proximal surface 580 of stop 578 and distal end 586 of ferrule 584 will result in a change to the depth of injections made with catheter 500. In the embodiment of FIG. 7 and FIG. 8, the travel of second elongate shaft 530 preferably stops when flange 576 contacts stop 578. Changes may be made in details, particularly in matters of shape, size, and arrangement of parts without exceeding the scope of the invention. The invention's scope is, of course, defined in the language in which the appended claims are expressed.

What is claimed is:

1. An injection catheter assembly comprising:
   a first elongated member having a proximal end, a distal end, and an external diameter;
   a second elongated member having a proximal region and a distal region,
      the second elongated member positioned at least partially within the first elongated member,
      the second elongated member having a piercing tip and being moveable with respect to the first elongated member, and
   a third elongated member,
      the third elongated member having a stop,
      the third elongated member positioned between the second elongated member and the first elongated member;
      the third elongated member defining a lumen along a portion of the length of the first elongated member,
      the third elongate member being rotatable with respect to the first elongate member, the degree of rotation of a first helical member of the third elongated member adjusting the distance that a piercing tip can extend from the distal end of the first elongated member,
      wherein the second elongated member has a flange and the distal travel of the flange is prevented beyond the stop.

2. The injection catheter assembly of claim 1 further comprising a second helical member to engage the first helical member.

3. The injection catheter assembly of claim 1 wherein the first helical member is positioned on an inner-surface of the third elongated member.

4. The injection catheter assembly of claim 1 wherein the first helical member is positioned at a distal end of the third elongated member.

5. The injection catheter assembly of claim 1 further comprising a second helical member to engage the first helical member, the second helical member having a lumen to receive the second elongated member therethrough.

6. The injection catheter assembly of claim 5 wherein the second helical member is integrally attached to a ferrule.

7. The injection catheter assembly of claim 5 wherein the first helical member has a distal end having a circumference greater than an outer-circumference of the second helical member.

8. The injection catheter assembly of claim 1 further comprising a header forming a distal contact surface, the header positioned at the distal end of the first elongated member.

9. The injection catheter assembly of claim 8 wherein the header has a radial enlargement.

10. The injection catheter assembly of claim 1 the second elongated member includes a lumen.

11. The injection catheter assembly of claim 1 the second elongated member defines a lumen along the entire length of the injection catheter assembly.

12. The injection catheter assembly of claim 1 further comprising a second helical member to engage the first helical member, the second helical member is integrally attached to a ferrule, the second helical member and the ferrule having lumens.

13. The injection catheter assembly of claim 1 wherein the stop is positioned between the flange and the first helical member.

* * * * *